United States Patent [19]

Irikura et al.

[11] Patent Number: 4,650,871
[45] Date of Patent: Mar. 17, 1987

[54] NOVEL SULFAMOYLBENZOIC ACID DERIVATIVES, PROCESS FOR THEIR PREPARATION

[75] Inventors: Tsutomu Irikura, Tokyo; Kyuya Okamura, Oomiya; Hideo Okubo; Hidemichi Mizuguchi, both of Nogi; Shigeru Yamanaka, Fujioka, all of Japan

[73] Assignee: Kyorin Pharmaceutical Co., Ltd., Tokyo, Japan

[21] Appl. No.: 804,123

[22] Filed: Dec. 3, 1985

[30] Foreign Application Priority Data

Dec. 4, 1984 [JP] Japan .................. 59-256877

[51] Int. Cl.⁴ .......................................... C07D 295/22
[52] U.S. Cl. ........................... 544/382; 544/377
[58] Field of Search ....................... 544/382, 377

[56] References Cited

U.S. PATENT DOCUMENTS 2,663,707 12/1953 Conroy et al. ............ 544/382
3,200,121 8/1965 Lovell ....................... 544/382
3,814,772 6/1974 Philippe .................... 544/382
4,267,175 5/1981 Watts ....................... 544/382

OTHER PUBLICATIONS

Chemical Abstracts, 58, 1469g, 1963.
Chemical Abstracts, 68, 105243p, 1968.
Chemical Abstracts, 69, 10473v, 1968.

Primary Examiner—Glennon H. Hollrah
Assistant Examiner—James H. Turnipseed
Attorney, Agent, or Firm—Oblon, Fisher, Spivak, McClelland & Maier

[57] ABSTRACT

This invention relates to sulfamoylbenzoic acid derivatives which possess diuretic and uricosuric activities, and which are of the formula (I)

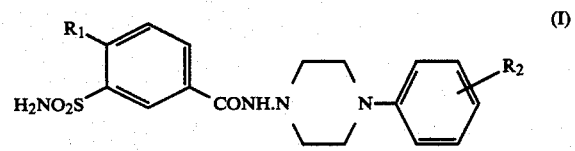

wherein $R_1$ is a chlorine atom or phenoxy group, $R_2$ is a hydrogen atom, halogen atom, lower alkyl group, lower alkoxy group or methylenedioxy group.

3 Claims, 1 Drawing Figure

NOVEL SULFAMOYLBENZOIC ACID DERIVATIVES, PROCESS FOR THEIR PREPARATION

DETAILED DESCRIPTION OF THE INVENTION

Figure 1:
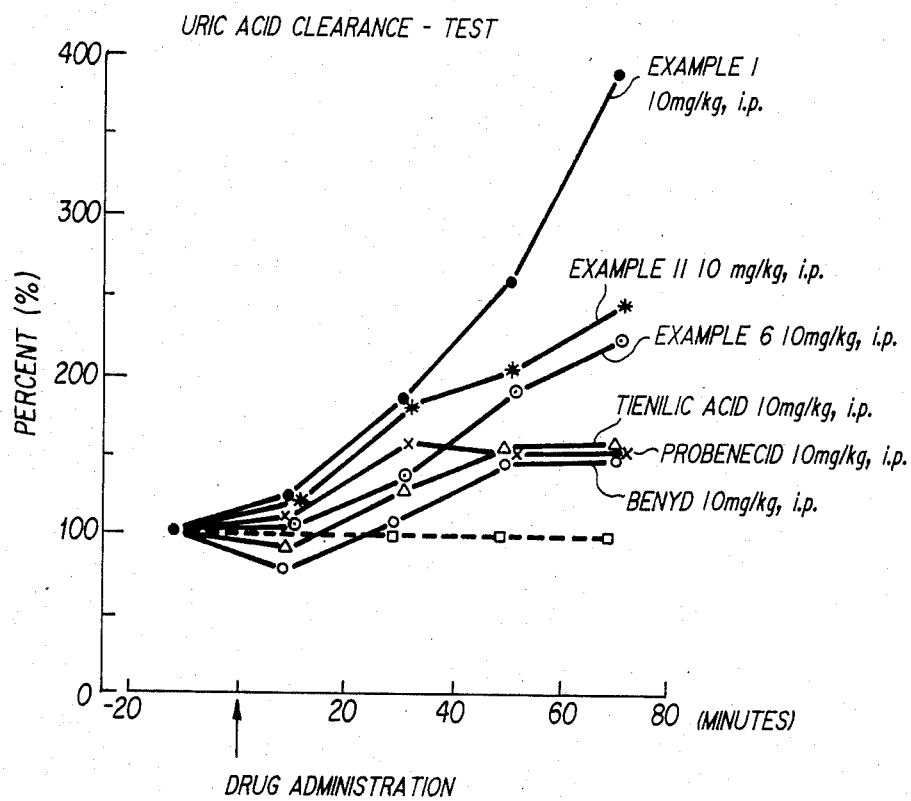

The present invention is concerned with certain novel sulfamoylbenzoic acid derivatives and process for their preparations. These derivatives possess potent saluretic, uricosuric and hypotensive activities. So that the compounds of this invention constitute valuable agents for medication of edema accompanied with liver disease or heart disease, especially heart failure, and for hypertension, hyperuricemia and so on.

Further details of this invention is concerned with new sulfamoylbenzoic acid derivatives of formula (I),

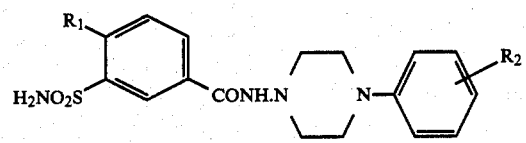

wherein $R_1$ is a chlorine atom or phenoxy group, $R_2$ is a hydrogen atom, halogen atom, lower alkyl, lower alkoxy, or methylenedioxy group, and with process for their preparations.

The compounds (I) of this invention can be prepared by reacting sulfamoylbenzoic acids (II) or their reactive derivatives with piperazine derivatives (III) in the presence of condensing agents.

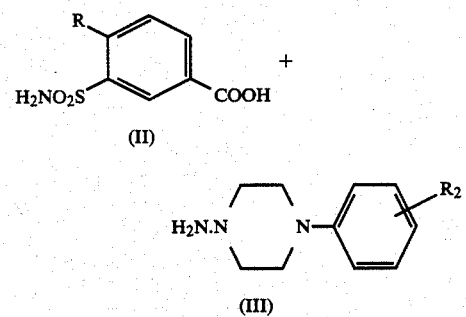

wherein $R_1$ and $R_2$ have the above-stated meanings.

The reaction of sulfamoylbenzoic acid derivatives (II) with piperazine derivatives (III) is carried out in the presence of condensing agents such as N,N'-dicyclohexylcarbodiimide, N,N'-carbonyldiimidazole, and so on.

This reaction is carried out by adding condensing agent to the mixture of compound (II) and (III). It is also convenient for the condensation that the compound (II) is at first converted to its acid anhydride in the presence of condensing agent and then the acid anhydride is reacted with compound (III). The suitable solvent of this reaction is aprotic solvent such as chloroform, tetrahydrofuran, dimethylformamide, and so on.

In the case of the reaction of reactive derivatives of sulfamoylbenzoic acids (II) with piperazine derivatives (III), acid chloride or acid bromide is used as reactive derivative. In such cases, triethylamine, pyridine, sodium carbonate, potassium carbonate, or the like is used as condensing agent, and benzene, toluene, chloroform, dichloromethane, tetrahydrofuran, or the like is used as solvent.

In order that the invention may be more fully understood, the following examples are given.

EXAMPLE 1

4-Chloro-N-[4-(2-methoxyphenyl)-1-piperazinyl]-3-sulfamoylbenzamide

To a solution of 1.8 g of N,N'-dicyclohexylcarbodiimide in 5 ml tetrahydrofuran was added a solution of 2.1 g of 4-chloro-3-sulfamoylbenzoic acid in 20 ml of tetrahydrofuran under stirring at room temperature. After the addition was completed, the mixture was stirred at room temperature for 20 minutes, then 0.83 g of 1-amino-4-(2-methoxyphenyl)piperazine was added, and the reaction mixture was stirred for 5 hours. Then 5 ml of 10% hydrochloric acid was added and stirred at room temperature for 10 minutes. 250 ml of 2% sodium hydroxide solution was added and insoluble materials were filtered off. The filtrate was alkalized with 2% sodium hydroxide solution to give white precipitate. The resulting precipitate was filtered, washed with water and recrystallized from ethanol to afford a title compound in a yield of 0.84 g (49%) as colorless crystals, mp 232°–235° C.

Analysis (%) for $C_{18}H_{21}ClN_4O_4S$, Calcd. (Found): C, 50.88 (51.06); H, 4.98 (5.02); N, 13.19 (13.19).

EXAMPLE 2

4-Chloro-N-[4-(2-methoxyphenyl)-1-piperazinyl]-3-sulfamoylbenzamide

To a mixture of 1 g of 1-amino-4-(2-methoxyphenyl)piperazine and 1 ml of triethylamine was added 1.25 g of 4-chloro-3-sulfamoylbenzoyl chloride under stirring at room temperature. The reaction mixture was stirred at room temperature for 9 hours. The resulting precipitate was filtered, washed with water and recrystallized from ethanol to afford a title compound in a yield of 1.20 g (60%) as colorless needle crystals, mp 231°–233° C.

Analysis (%) for $C_{18}H_{21}ClN_4O_4S$, Calcd. (Found): C, 50.88 (50.58); H, 4.98 (5.19); N, 13.19 (13.15).

Other new compounds prepared by same procedure as in Example 2 are listed in Table 1.

TABLE 1

| Example No. | $R_1$ | $R_2$ | mp (°C.) | Yield (%) | Analysis (%) Calcd./Found C | H | N |
|---|---|---|---|---|---|---|---|
| 3 | Cl | 2-CH$_3$ | 253–255 | 33.3 | 52.87 52.64 | 5.17 5.15 | 13.70 13.66 |
| 4 | Cl | H | 255–257 | 30.2 | 51.71 51.78 | 4.85 4.76 | 14.19 14.15 |
| 5 | Cl | 2-iso-Pr | 190–192 | 22.5 | 53.39 53.22 | 5.91 5.63 | 12.46 12.34 |
| 6 | Cl | 3-OCH$_3$ | 267–269 | 30.0 | 50.88 50.79 | 4.98 4.97 | 13.19 13.08 |
| 7* | Cl | 2-Cl | 149–151 | 40.0 | 46.94 46.91 | 4.41 4.32 | 12.86 12.87 |
| 8** | Cl | 2-F | 245–247 | 34.1 | 49.49 49.38 | 4.02 4.46 | 13.58 13.31 |
| 9 | Cl | 3,4-OCH$_2$O— | 270 | 50.8 | 49.26 49.13 | 4.36 4.30 | 12.77 12.65 |
| 10*** | O—Ph | 2-OCH$_3$ | 211–214 | 3.6 | 58.86 59.17 | 5.51 5.39 | 11.44 11.06 |

TABLE 1-continued $$\underset{H_2NO_2S}{\overset{R_1}{\bigcirc}}\text{CONH.N}\overset{}{\bigcirc}N\overset{R_2}{\bigcirc} \quad (I)$$

| Example No. | $R_1$ | $R_2$ | mp (°C.) | Yield (%) | Analysis (%) Calcd./Found C H N |
|---|---|---|---|---|---|
| 11 | Cl | 4-OCH$_3$ | 245–247 | 62.7 | 48.82 5.45 12.65 / 49.10 5.17 12.66 |

*⅓ H$_2$O,
**1/9 H$_2$O,
***2/5 H$_2$O.

The experiments to prove usefulness of the present compounds are shown as follows.

EXPERIMENT 1

Diuretic and saluretic effects

Male Wistar strain rats weighing about 300 g were used. Each group was consisted of 5 animals. After deprivation of food and water for 18 hours, the compound of the present invention and the reference drugs were administered orally. Results are shown in Table 2. The compounds of Example 1 and 6 are potent diuretic agents, and show saluretic property in nature.

TABLE 2

| | | Diuretic and saluretic effects | |
|---|---|---|---|
| | | 0–5 hrs | 0–24 hrs |
| Control (Saline) | Na$^+$ | 1.43 ± 0.18 | 2.89 ± 0.25 |
| | K$^+$ | 1.15 ± 0.15 | 4.01 ± 0.09 |
| | UV | 23.8 ± 1.78 | 41.8 ± 1.78 |
| Example 1 (25 mg/kg, p.o.) | Na$^+$ | 3.85 ± 0.28** | 6.66 ± 0.29** |
| | K$^+$ | 1.33 ± 0.07 | 4.88 ± 0.22** |
| | UV | 36.1 ± 4.14* | 63.1 ± 2.13** |
| Behyd (25 mg/kg, p.o.) | Na$^+$ | 4.48 ± 0.53** | 7.98 ± 0.87** |
| | K$^+$ | 1.57 ± 0.19 | 5.62 ± 0.43* |
| | UV | 42.5 ± 4.51* | 72.0 ± 6.71** |
| HCT (25 mg/kg, p.o.) | Na$^+$ | 5.24 ± 0.47** | 7.75 ± 0.60** |
| | K$^+$ | 1.69 ± 0.20 | 5.45 ± 0.55 |
| | UV | 42.9 ± 3.31** | 66.6 ± 4.31** |
| Control (Saline) | Na$^+$ | 0.56 ± 0.14 | 2.67 ± 0.07 |
| | K$^+$ | 0.31 ± 0.05 | 1.72 ± 0.12 |
| | UV | 19.8 ± 2.03 | 28.7 ± 1.97 |
| Example 6 (10 mg/kg, p.o.) | Na$^+$ | 1.52 ± 0.18** | 4.15 ± 0.25** |
| | K$^+$ | 0.65 ± 0.06** | 2.12 ± 0.11* |
| | UV | 26.6 ± 2.74 | 38.9 ± 2.00** |

Na$^+$, K$^+$: Total excretion of sodium and potassium (mEq/kg).
UV: Urine volume (ml/kg).
Behyd: Benzylhydrochlorothiazide.
HCT: Hydrochlorothiazide.
*, **Different from the control, p < 0.05, p < 0.01, respectively.

EXPERIMENT 2

Uricosuric effect

Clearance experiments were done on 11–14 weeks old male Wistar strain rats. Each group was consisted of 5 animals. Uricosuric activity was evaluated by clearance ratio (uric acid clearance/inulin clearance). Results are shown in FIG. 1. It is obvious that the compound of Example 1 has a more potent uricosuric effect than probenecid known as uricosuric agent.

EXPERIMENT 3

Hypouricemic effet in acutely uric acid loaded rats

Ten week old male Wistar strain rats were used in this experiment. Rats had been administered intraperitoneally with uric acid at a dose of 200 mg/kg at 30 minutes before the drug administration. The compound of Example 1 and probenecid were administered intraperitoneally. Thirty minutes later, the animals were killed by exsanguination. Blood was collected and then serum uric acid levels were measured. Table 3 shows that the compound of Example 1 also has a hypouricemic activity.

TABLE 3

| Serum uric acid levels in acutely uric acid loaded rats | | | |
|---|---|---|---|
| | Dose (mg/kg, i.p.) | Serum uric acid (mg/dl) | Ratio | N |
| Saline | | 1.27 ± 0.11 | 1 | 8 |
| Probenecid | 10 | 1.88 ± 0.31 | 1.45 | 5 |
| | 100 | 0.79 ± 0.14* | 0.62 | 4 |
| Behyd | 10 | 1.15 ± 0.16 | 0.91 | 5 |
| Example 1 | 10 | 0.90 ± 0.08* | 0.71 | 5 |

*Different from the saline, p < 0.05.

EXPERIMENT 4

Hypotensive effect

Daily oral administration of the compound of Example 1 at a dose of 100 mg/kg for 4 days lowered the systolic blood pressure of spontaneously hypertensive rats. Data are shown in Table 4.

TABLE 4

| Hypotensive effect | | | |
|---|---|---|---|
| | Systolic blood Pressure (mmHg) | Heart rate (beats/min) | N |
| Saline | 178 ± 3.5 | 403 ± 13 | 3 |
| Example 1 (100 mg/kg, p.o. × 4 days) | 158 ± 3.9* | 417 ± 9 | 3 |

*Different from the saline group, p < 0.05.

EXPERIMENT 5

Acute toxicity

Non of ICR strain mice died after an oral administration of the compound of Example 1 at a dose of 2,500 mg/kg.

Explanation of FIG. 1.

FIG. 1 shows uricosuric activity of the compound of Example 1 and other drugs. Ordinate means percent change of uricosuric activity against saline group control. Abscissa means time (minutes) after the drug administration.

What is claimed is:

1. A sufamoylbenzoic acid derivative of formula (I);

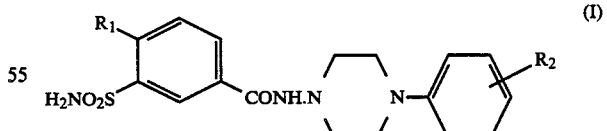

wherein $R_1$ is a chlorine atom or phenoxy group, $R_2$ is a hydrogen atom, halogen atom, lower alkyl group, lower alkoxy group or methylenedioxy group.

2. The derivative of claim 1, where $R_1$ is chlorine and $R_2$ is 2-methoxy.

3. The derivative of claim 1, wherein $R_1$ is chlorine and $R_2$ is 3-methoxy.

* * * * *